US00PP32679P3

(12) United States Plant Patent
Post

(10) Patent No.: US PP32,679 P3
(45) Date of Patent: Dec. 22, 2020

(54) ***CHRYSANTHEMUM* PLANT NAMED 'DLFZEMB5'**

(50) Latin Name: ***Chrysanthemum* X *morifolium***
Varietal Denomination: DLFZEMB5

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 16/873,322

(22) Filed: Mar. 19, 2020

(65) Prior Publication Data

US 2020/0305325 P1 Sep. 24, 2020

Related U.S. Application Data

(60) Provisional application No. 62/919,611, filed on Mar. 20, 2019.

(51) Int. Cl.
*A01H 6/14* (2018.01)
*A01H 5/02* (2018.01)

(52) U.S. Cl.
USPC ..... Plt./289
CPC ..... *A01H 6/1424* (2018.05)

(58) Field of Classification Search
USPC ..... Plt./289
See application file for complete search history.

(56) References Cited

PUBLICATIONS

PLUTO Plant Variety Database Aug. 19, 2020.*

* cited by examiner

*Primary Examiner* — Annette H Para
(74) *Attorney, Agent, or Firm* — C. A. Whealy

(57) ABSTRACT

A new and distinct cultivar of *Chrysanthemum* plant named 'DLFZEMB5', characterized by its upright plant habit; vigorous growth habit; large dark green-colored leaves; uniform flowering habit; strong upright flowering stems typically grown as a single-stem (disbudded) cut flower; decorative-type inflorescences with light yellow green and yellow green bi-colored ray florets; and relative resistance to *Fusarium oxysporum* f. sp. *chrysanthemi.*

2 Drawing Sheets

Figure 1:
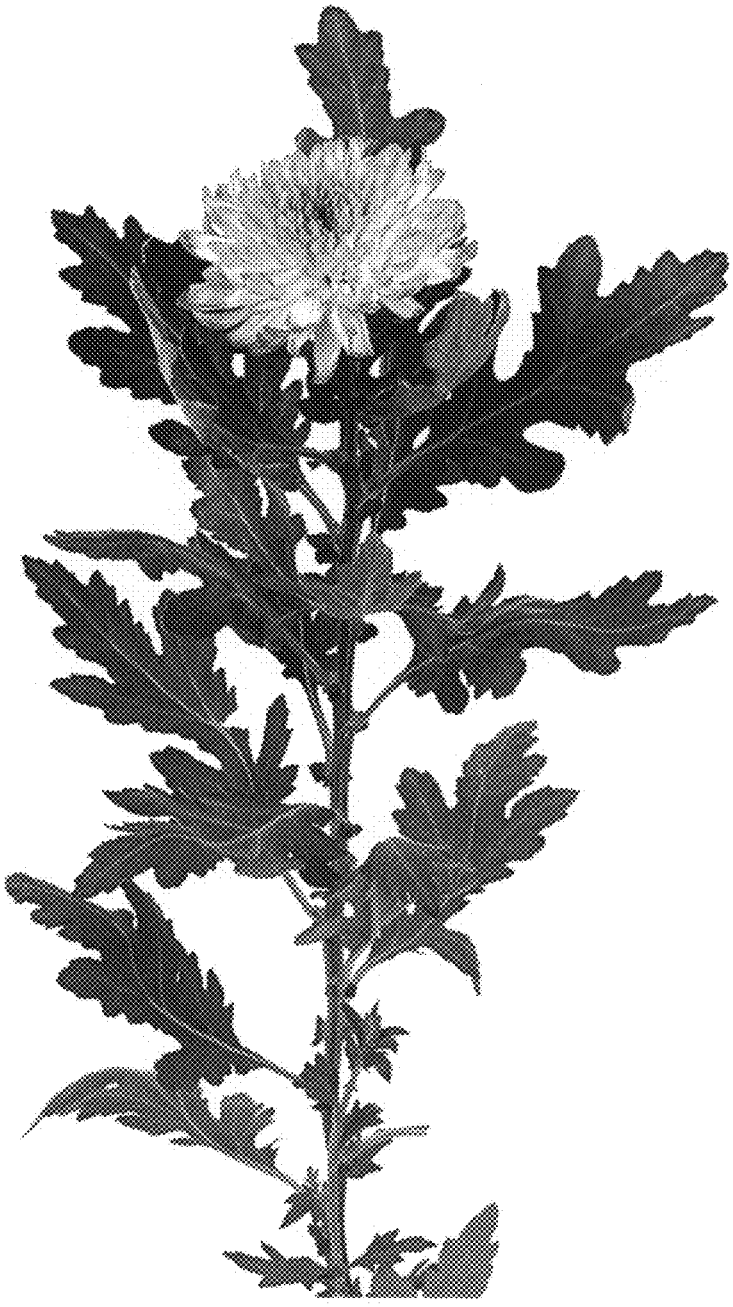

Botanical designation: *Chrysanthemum* X *morifolium.*
Cultivar denomination: 'DLFZEMB5'.

CROSS-REFERENCED TO CLOSELY-RELATED APPLICATIONS

Title: Varieties of *Chrysanthemum* Plants
Inventor/Applicant: Arie Gerard Post
Filed: Mar. 20, 2019
Ser. No.: 62/919,611
Inventor/Applicant hereby claim the benefit of this provisional U.S. Patent Application.

STATEMENT REGARDING PRIOR DISCLOSURES BY INVENTOR/APPLICANT & ASSIGNEE

An European Community Plant Breeder's Rights application for the instant plant was filed by the Assignee, Deliflor Royalties B.V. of Maasdijk, The Netherlands on Apr. 5, 2018, application number 2018/0952 and a Columbian Plant Breeder's Rights application was filed on Aug. 24, 2018, application number A182422. Foreign priority is not claimed to these applications.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFZEMB5'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant is a naturally-occurring whole plant mutation of *Chrysanthemum* x *morifolium* 'Zembla', disclosed in U.S. Plant Pat. No. 14,052. The new *Chrysanthemum* plant was discovered and selected as a single flowering plant from within a population of plants of 'Zembla' in a controlled greenhouse environment in Maasdijk, The Netherlands in October, 2016.

Asexual reproduction of the new *Chrysanthemum* plant by vegetative terminal cuttings since October, 2016 in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFZEMB5'. These characteristics in combination distinguish 'DLFZEMB5' as a new and distinct *Chrysanthemum* plant:

1. Upright plant habit; vigorous growth habit.
2. Large dark green-colored leaves.
3. Uniform flowering habit.
4. Strong upright flowering stems typically grown as a single-stem (disbudded) cut flower.
5. Decorative-type inflorescences with light yellow green and yellow green bi-colored ray florets.
6. Relatively resistant to *Fusarium oxysporum* f. sp. *chrysanthemi*.

Plants of the new *Chrysanthemum* differ from plants of the mutation parent, 'Zembla', in ray floret color as plants of the new *Chrysanthemum* have light yellow green and yellow green bi-colored ray florets whereas plants of 'Zembla' have solid yellow green-colored ray florets.

Plants of the new *Chrysanthemum* can be compared to plants of *Chrysanthemum* X *morifolium* 'Zembla Lime', not patented. In side-by-side comparisons, plants of the new *Chrysanthemum* differ primarily from plants of 'Zembla Lime' in ray floret color as ray florets of plants of the new *Chrysanthemum* are darker yellow green in color than ray florets of plants of 'Zembla Lime'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1 of 2) comprises a side perspective view of a typical flowering stem of 'DLFZEMB5' grown as a disbud-type cut flower.

Figure 2:
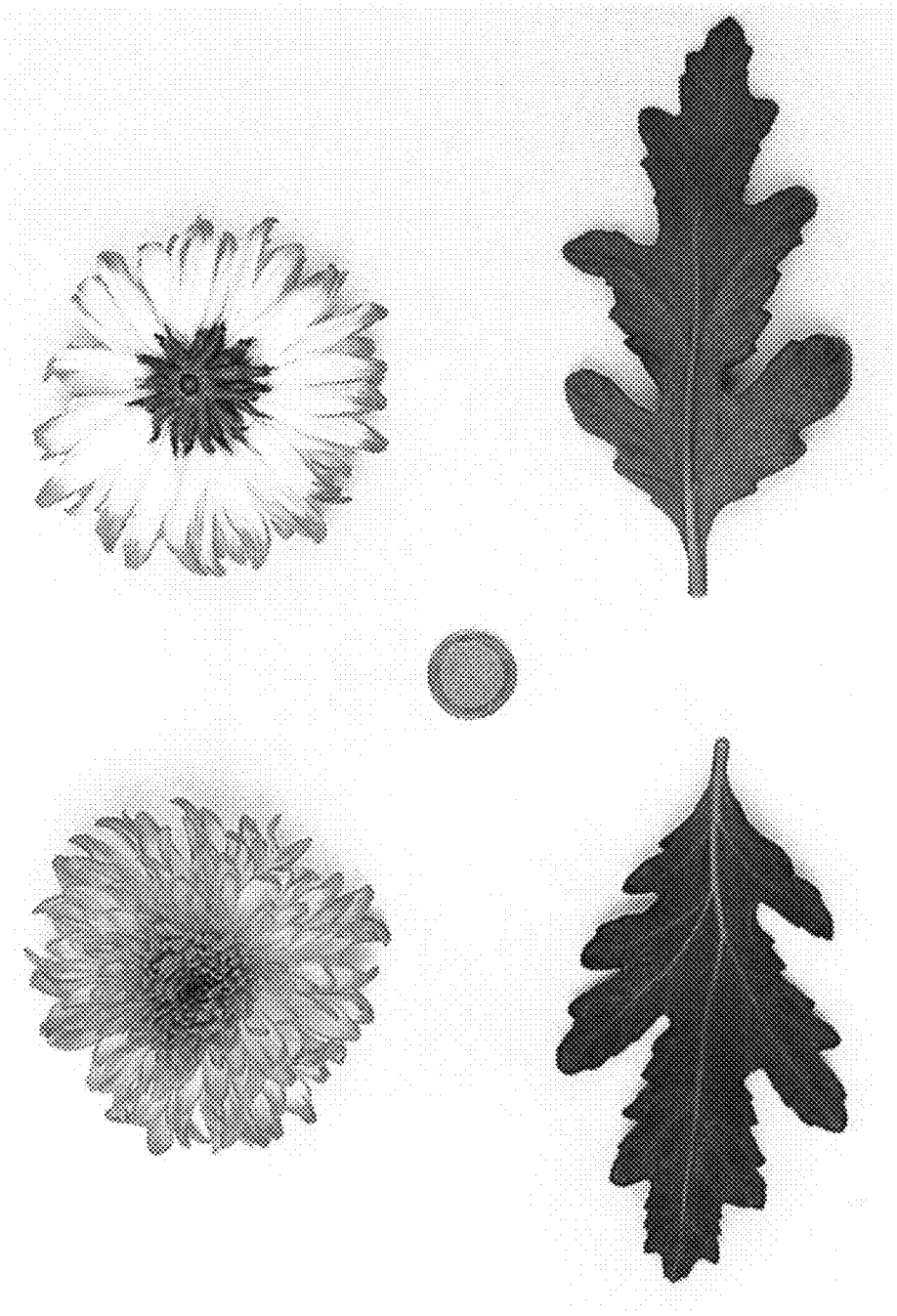

The photograph on the second sheen (FIG. 2 of 2) is a close-up view of lower (top of the photographic sheet) and upper (bottom of the photographic sheet) surfaces of typical inflorescences (left) and leaves (right).

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 2° C. to 20° C. and light levels averaged 8 klux. Plants were grown as single-stem disbud-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFZEMB5'.

Parentage: Naturally-occurring whole plant mutation of *Chrysanthemum* X *morifolium* 'Zembla', disclosed in U.S. Plant Pat. No. 14,052.

Propagation:

*Type*.—Terminal vegetative cuttings.

*Time to initiate roots, summer*.—About six days at temperatures about 24° C.

*Time to initiate roots, winter*.—About eight days at temperatures about 22° C.

*Time to produce a rooted young plant, summer*.—About twelve days at temperatures about 24° C.

*Time to produce a rooted young plant, winter*.—About two weeks at temperatures about 22° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem disbud-type; upright plant habit; vigorous growth habit and rapid growth rate.

*Plant height, soil level to top of foliar plane*.—About 83.8 cm.

*Plant height, soil level to top of inflorescence plane*.—About 87.6 cm.

*Plant diameter*.—About 22.4 cm.

*Flowering stem length*.—About 77.7 cm.

*Flowering stem diameter*.—About 6 mm.

*Flowering stem internode length*.—About 3 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 144A to 144B.

*Flowering stem color, developed*.—Close to 146B.

*Leaf description*.—Arrangement: Alternate; simple. Length: About 15.1 cm. Width: About 8.6 cm. Shape: Oblong to obovate. Apex: Short apiculate. Base: Attenuate. Margin: Palmately lobed, coarsely serrate to crenate; sinuses convergent and deep. Texture and luster, upper surface: Moderately pubescent, not rugose; moderately velvety; matte to slightly glossy. Texture and luster, lower surface: Moderately pubescent, prominent venation; slightly velvety; matte. Venation pattern: Pinnate, reticulate. Color: Developing leaves, upper surface: Close to between 143B and 144A. Developing leaves, lower surface: Close to 138B. Fully developed leaves, upper surface: Close to between NN137A and 147A; venation, close to 146B. Fully developed leaves, lower surface: Close to 147B; venation, close to between 146C and 147B. Petioles: Length: About 2.4 cm. Diameter: About 2.75 mm by 3 mm. Strength: Moderately strong. Texture and luster, upper and lower surfaces: Densely pubescent; slightly glossy. Color, upper surface: Close to 146B; edges, close to 137A. Color, lower surface: Close to 147C; edges, close to 137A. Stipules: Quantity and appearance: Two leafy stipules, opposite, at the petiole attachment to the stem. Length: About 4 mm. Width: About 9 mm. Shape: Roughly reniform. Texture and luster, upper surface: Moderately pubescent, not rugose; moderately velvety; matte to slightly glossy. Texture and luster, lower surface: Moderately pubescent, prominent venation; slightly velvety; matte. Color, upper surface: Close to between NN137A and 147A. Color, lower surface: Close to 147B.

Inflorescence description:

*Appearance*.—Decorative uncurved inflorescence form with oblanceolate-shaped ray florets and tubular disc florets (disc florets are inconspicuous); inflorescences borne perpendicular to peduncles and face mostly upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 53 days later when grown as a disbud-type.

*Postproduction longevity*.—Good postproduction longevity; in an interior environment, inflorescences and foliage will maintain good color and substance for about two weeks; inflorescences persistent.

*Quantity of inflorescences*.—Grown as a disbud-type, all lateral inflorescences are physically removed and only the terminal inflorescence is allowed to develop; if grown as a spray-type, then typically about 18 inflorescences will develop.

*Inflorescence size*.—Diameter: Grown as a disbud type, about 10.5 cm and grown as a spray-type, about 8.2 cm. Depth (height): Grown as a disbud type, about 6.2 cm and grown as a spray-type, about 3.7 cm. Disc diameter: About 5 mm.

*Receptacles*.—Height: About 5 mm. Diameter: About 1.1 cm. Shape: Flattened globular. Color: Close to 145C to 145D.

*Inflorescence buds*.—Height: About 1.9 cm. Diameter: About 1.4 cm. Shape: Oblong. Texture and luster: Distally, smooth and glabrous; proximally, slightly to moderately pubescent; slightly glossy. Color: Close to 143A; immature ray florets, close to 145D and 145B.

*Ray florets*.—Quantity and arrangement: About 340 arranged in about eight whorls. Length: About 4 cm; varying between 1.6 cm and 5.2 cm. Width: About 9 mm; varying between 0.2 cm and 1.2 cm. Shape: Oblanceolate; slightly convex and moderately carinate. Apex: Obtuse to rounded. Base: Attenuate. Margin: Entire; slightly and coarsely undulate. Aspect: Initially upright to about 90° from vertical. Texture and luster, upper and lower surfaces: Smooth, glabrous; moderately velvety; matte. Color: When opening, upper and lower surfaces: Close to NN155B; distally, close to 145B to 145C. Fully opened, upper surface: Close to NN155C; distally, close to 145B to 145C; venation, similar to lamina colors; color does not change with development. Fully opened, lower surface: Close to NN155C; distally, close to 145B; venation, similar to lamina; color does not change with development.

*Disc florets*.—Quantity and arrangement: About 18 arranged in about three whorls; disc florets inconspicuous. Length: About 7 mm. Diameter: About 1 mm. Shape: Lower 85% fused into a tube; upper 15% free. Apex: Narrowly acute. Margin, distally: Entire. Texture and luster, inner and outer surfaces: Smooth, glabrous; glossy. Color, when opening, inner and outer surfaces: Close to 150D; towards the apex, close to N144D and towards the base, close to 145D. Color, fully opened, inner and outer surfaces: Close to 150D; towards the apex, close to N144D and towards the base, close to 145D,

*Involucral bracts*.—Quantity and arrangement: About 32 arranged in three whorls. Length: About 1.2 cm. Width: About 3.5 mm. Shape: Narrowly ovate. Apex: Obtuse. Base: Cuneate. Margin: Entire. Texture and luster, upper surface: Smooth, glabrous; glossy. Texture and luster, lower surface: Moderately pubescent; matte. Color, upper surface: Close to between 143A and 144A; margins, translucent and close to 157A and 200B. Color, lower surface: Close to 137B; margins, translucent and close to 157A and 200B.

*Peduncles*.—Length, terminal peduncle: About 7.1 cm. Diameter, terminal peduncle: About 4 mm. Length, third peduncle (when grown as a spray-type): About 8.6 cm. Diameter, third peduncle (when grown as a spray-type): About 3 mm. Strength: Strong. Aspect, terminal peduncle: Mostly upright. Aspect, third peduncle (when grown as a spray-type): About 40° from the flowering stem axis. Texture and luster: Moderately pubescent; moderately glossy. Color: Close to 143A.

*Reproductive organs*.—Androecium: Present on disc florets only. Quantity: About five per floret. Filament length: About 2 mm. Filament color: Close to 150D. Anther size: About 0.5 mm by 2 mm. Anther shape: Narrowly oblong. Anther color: Close to 13A. Pollen amount: Scarce. Pollen color: Close to 14B. Gynoecium: Present on both ray and disc florets. Quantity: One per ray floret. Pistil length: About 7 mm. Style length: About 5.75 mm. Style color: Close to 145C. Stigma diameter: About 1 mm. Stigma shape: Cleft, decurrent. Stigma color: Close to 153D. Ovary color: Close to 145D.

*Seeds and fruits*.—To date, seed and fruit production have not been observed on plants of the new *Chrysanthemum*.

Pathogen & pest resistance: Plants of the new *Chrysanthemum* have been observed to be relatively resistant to *Fusarium oxysporum* f. sp. *chrysanthemi*. To date, plants of the new *Chrysanthemum* have not been observed to be resistant to pests and other pathogens common to plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFZEMB5' as illustrated and described.

* * * * *